(12) United States Patent
Donnelly et al.

(10) Patent No.: US 9,301,528 B2
(45) Date of Patent: Apr. 5, 2016

(54) SYNERGISTIC COMBINATION OF A LENACIL COMPOUND AND ONE OF DCOIT OR OIT FOR DRY FILM PROTECTION

(71) Applicants: Rohm and Haas Company, Philadelphia, PA (US); Dow Global Technologies LLC, Midland, MI (US)

(72) Inventors: Kenneth M. Donnelly, Bensalem, PA (US); Pierre Marie Alain Lenoir, Richterswil (CH); Lukas Thomas Johannes Villiger, Buchs (CH)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/646,786

(22) PCT Filed: Nov. 29, 2013

(86) PCT No.: PCT/US2013/072455
§ 371 (c)(1),
(2) Date: May 22, 2015

(87) PCT Pub. No.: WO2014/085738
PCT Pub. Date: Jun. 5, 2014

(65) Prior Publication Data
US 2015/0335019 A1   Nov. 26, 2015

Related U.S. Application Data

(60) Provisional application No. 61/731,665, filed on Nov. 30, 2012.

(51) Int. Cl.
*A01N 43/54* (2006.01)
*A01N 43/80* (2006.01)
*A01P 1/00* (2006.01)
*C09D 5/14* (2006.01)
*A01N 25/34* (2006.01)

(52) U.S. Cl.
CPC ............ *A01N 43/54* (2013.01); *A01N 25/34* (2013.01); *A01N 43/80* (2013.01); *C09D 5/14* (2013.01)

(58) Field of Classification Search
CPC .......... A01N 43/54; A01N 43/80; A01P 1/00
USPC ....................................... 514/258.1
See application file for complete search history.

(56) References Cited

U.S. PATENT DOCUMENTS

| 5,292,763 A | 3/1994 | Hsu |
| 2012/0115887 A1 | 5/2012 | Sianawati |

FOREIGN PATENT DOCUMENTS

DE   3836332 A1   4/1990

OTHER PUBLICATIONS

Kappock, et al., "Protecting Paints", EP Coating Journal, p. 144 (2005).
Markarian, et al., "Steady growth predicted for biocides", Plastics Additives and Compounding, vol. 8, No. 1, pp. 30-33 (2006).
Jurgen, et al., "Analyzing Cytotoxic Effects of Selected Isothiazol-3-one Biocides Using the Toxic Ratio Concept and Structure-Activity Relationship", Chem. Research in Toxicology, vol. 22, No. 12, pp. 1954-1961 (2009).
Burkhardt, et al., "Leaching of Biocides from Facades under Natural Weather Conditions", vol. 46., No. 10, pp. 5497-5503 (2012).
"521: lenacil" In: "The Pesticide Manual Fifteenth Edition", British Crop Protection Council, pp. 692-693 (2009).

*Primary Examiner* — Yevegeny Valenrod
(74) *Attorney, Agent, or Firm* — Tifani M. Edwards

(57) ABSTRACT

A synergistic antimicrobial composition containing lenacil and one of 4,5-dichloro-2-n-octyl-4-isothiazolin-3-one or 2-n-octyl-4-isothiazolin-3-one is provided. Also provided is a method of inhibiting the growth of or controlling the growth of microorganisms in a building material by adding such a synergistic antimicrobial composition. Also provided is a coating composition containing such a synergistic antimicrobial composition, and a dry film made from such a coating composition.

7 Claims, No Drawings

SYNERGISTIC COMBINATION OF A LENACIL COMPOUND AND ONE OF DCOIT OR OIT FOR DRY FILM PROTECTION

This invention relates to combinations of antimicrobial compounds and their uses in dry film protection applications, the combinations having unexpectedly greater activity than would be expected for the use of both of the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, e.g., those resistant to some antimicrobial compounds. Combinations of different antimicrobial compounds are sometimes used to provide overall control of microorganisms in a particular end use environment. For example, WO 1998/121962 discloses combinations of 3-iodo-2-propynyl-butylcarbamate and pyrithione, but this reference does not suggest any of the combinations claimed herein. Moreover, there is a need for additional combinations of antimicrobial compounds with relatively low impact on health and/or the environment. The problem addressed by this invention is to provide such additional combinations of antimicrobial compounds.

Antimicrobial compounds are sometimes included in liquid coating compositions that are applied to a substrate and that become dry films. It is desirable that such dry films control surface fungi and algae and that such dry films also present as little adverse effect as possible on health and the environment.

In the present invention there is provided a synergistic antimicrobial composition comprising lenacil and one of 4,5-dichloro-2-n-octyl-4-isothiazolin-3-one or 2-n-octyl-4-isothiazolin-3-one.

The invention further provides a method of inhibiting the growth of or controlling the growth of microorganisms in a building material, the method comprising the step of adding a synergistic antimicrobial composition comprising lenacil and one of 4,5-dichloro-2-n-octyl-4-isothiazolin-3-one or 2-n-octyl-4-isothiazolin-3-one; wherein the weight ratio of the 4,5 dichloro-2-n-octyl-4-isothiazolin-3-one or 2-n-octyl-4-isothiazolin-3-one to lenacil is from 1:5 to 5:1.

The present invention further comprises a coating composition comprising a synergistic antimicrobial composition comprising lenacil and one of 4,5-dichloro-2-n-octyl-4-isothiazolin-3-one or 2-n-octyl-4-isothiazolin-3-one. The coating composition of the present invention may also comprise a synergistic antimicrobial composition comprising lenacil and one of 4,5-dichloro-2-n-octyl-4-isothiazolin-3-one or 2-n-octyl-4-isothiazolin-3-one; wherein the weight ratio of the 4,5 dichloro-2-n-octyl-4-isothiazolin-3-one or 2-n-octyl-4-isothiazolin-3-one to lenacil is from 1:5 to 5:1.

Lastly, the present invention provides a dry film made by a process comprising applying a layer of the coating composition comprising a synergistic antimicrobial composition comprising lenacil and one of 4,5-dichloro-2-n-octyl-4-isothiazolin-3-one or 2-n-octyl-4-isothiazolin-3-one; wherein the weight ratio of the 4,5 dichloro-2-n-octyl-4-isothiazolin-3-one or 2-n-octyl-4-isothiazolin-3-one to lenacil is from 1:5 to 5:1 to a substrate and drying the coating composition or allowing the coating composition to dry.

The following is a detailed description of the invention.

As used herein, the following terms have the designated definitions, unless the context clearly indicates otherwise.

The term "antimicrobial compound" refers to a compound capable of inhibiting the growth of or controlling the growth of microorganisms; antimicrobial compounds include bactericides, bacteriostats, fungicides, fungistats, algaecides and algistats, depending on the dose level applied, system conditions and the level of microbial control desired. Such term "antimicrobial compound" as used herein is synonymous with the term "biocide".

The term "microorganism" includes, for example, fungi (such as yeast and mold), bacteria and algae.

The following abbreviations are used throughout the specification: ppm=parts per million by weight (weight/weight), mL=milliliter, ATCC=American Type Culture Collection, SAG=Culture Collection of Algae at Goettingen University, CCAP=Culture Collection of Algae and Protozoa and MIC=minimum inhibitory concentration.

Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present.

As used herein, "DCOIT" is 4,5-dichloro-2-n-octyl-4-isothiazolin-3-one (CAS registry number 64359-81-5), "OIT" is 2-n-octyl-4-isothiazolin-3-one (CAS registry number 26530-20-1), and "IT" is 4-isothiazolin-3-one.

When a ratio is the herein to be "X:1 or higher," it is meant that the ratio is Y:1, where Y is X or greater, and when a ratio is the herein to be "X:1 or lower," it is meant that the ratio is Z:1, where Z is X or less. The same logic follows for ratios that are "1:X or higher" and "1:X or lower".

Lenacil belongs to the class of uracil herbicides, 3-cyclohexyl-1,5,6,7-tetrahydrocyclopentapyrimidine-2,4(3H)-dione ($C_{13}H_{18}N_2O_2$) (CAS registry number 2164-08-1). Lenacil is a known herbicide that is approved in many jurisdictions as a soil-acting herbicide for the control of grass and broadleaved weeds in beet and other crops.

Lenacil has relatively low solubility in water. This relatively low solubility in water is preferred for an antimicrobial material that may be included in a coating composition or other building material, because dried coatings and building materials are exposed to water, which could tend to remove a highly soluble compound from the dried coating or the building material.

The present invention involves a composition that contains both lenacil and one of 4,5-dichloro-2-n-octyl-4-isothiazolin-3-one or 2-n-octyl-4-isothiazolin-3-one. It has been surprisingly found that such a composition is synergistically effective as a biocide. It has been especially surprisingly found that compositions that contain both lenacil and one of DCOIT or OIT are synergistically effective as biocides.

When DCOIT is present, preferably the weight ratio of DCOIT to lenacil compound is preferably 1:5 to 5:1. When OIT is present, preferably the weight ratio of OIT to lenacil compound is 1:5 to 5:1.

If a formulation contains both DCOIT and OIT, it is useful to consider the sum of the weights of all the listed IT compounds (i.e., the sum of the weight of DCOIT plus the weight of OIT. The preferred ratio of the sum of the weights of all the listed IT compounds to the weight of lenacil compound is 1:10 to 10:1.

The mixture of lenacil and one of DCOIT or OIT may be included in a coating composition. Lenacil and one of DCOIT or OIT may be added to the coating composition separately or as a mixture or any combination thereof. Preferred coating compositions are liquid. Coating compositions may be aqueous or non-aqueous. Aqueous coating compositions generally contain 30% or more water by weight of the mixture, based on the weight of the coating composition.

Among embodiments in which lenacil and one of DCOIT or OIT are included in paint or other coating composition, preferred coating compositions are liquid compositions, especially compositions that contain dispersions of polymers in aqueous media.

In addition to paints and other coating compositions such as marine anti-fouling, the antimicrobial compound combinations of the present invention are particularly useful in preservation of building materials, e.g., adhesives, caulk, joint compound, sealant, wallboard, etc., polymers, plastics, synthetic and natural rubber, paper products, fiberglass sheets, insulation, exterior insulating finishing systems, roofing and flooring felts, building plasters, bricks, mortar, gypsum board, wood products and wood-plastic composites. When an antimicrobial compound combination of the present invention is present in a building material, it is preferred that some or all of the antimicrobial compound combination is present at the surface of the building material or near enough to the surface of the building material to inhibit microbial growth on that surface.

In some embodiments, latex paints or other liquid coating compositions are used that contain the antimicrobial compound combinations disclosed herein.

Coating compositions are designed so that a layer of the coating composition can readily be applied to a substrate and then dried or allowed to dry to form a dry film. Coating compositions contain a binder. Binders contain one or more of the following: one or more polymer, one or more oligomer, and/or one or more monomer. Oligomers and monomers in binders are designed to polymerize and/or crosslink during or after the formation of the dry film. Polymers in a binder may or may not be designed to crosslink during or after the formation of the dry film.

Coating compositions optionally contain one or more pigment. A pigment is a mineral or an organic substance in the form of small solid particles. Pigments provide full or partial opacity to the dry film.

The antimicrobial compound combinations are useful for preservation of the dry film coating resulting after application of paint or other liquid coating composition. Preferably, the antimicrobial composition is an aqueous latex paint comprising one or more of the antimicrobial compound combinations disclosed herein, or the dry film coating resulting from application of the paint to a surface. An aqueous latex paint is an aqueous liquid coating composition in which the binder is a polymer in the form of a latex (i.e., in the form of polymer particles dispersed throughout the water). More preferred are aqueous latex paints in which the binder contains one or more acrylic polymer.

Typically, the amount of the antimicrobial compound combinations of the present invention to control the growth of microorganisms is from 100 ppm to 10,000 ppm active ingredient. For example, in the present invention, lenacil plus OIT and/or DCOIT is present in an amount from 100 ppm to 10,000 ppm. The antimicrobial combinations of the composition are present in an amount of at least 100 ppm and no more than 8,000 ppm, preferably no more than 6,000 ppm, preferably no more than 5,000 ppm, preferably no more than 4,000 ppm no more than 3,000 ppm, preferably no more than 2500 ppm, and preferably no more than 2,000 ppm. Concentrations mentioned above are in a liquid coating composition, such as paint, containing the antimicrobial compound combinations; antimicrobial compound combination levels in the dry film coating will be higher.

The present invention also encompasses a method for preventing microbial growth in building materials, especially in dry film coatings, by incorporating any of the claimed antimicrobial compound combinations into the materials.

Typically, the antimicrobial compositions are used to inhibit growth of algae and/or fungi.

The composition of the present invention contains lenacil and one of DCOIT or OIT. It is contemplated that some embodiments may contain one or more additional antimicrobial compound.

The following are examples of the present invention.

Sample preparation for antimicrobial testing was performed as follows:

Slurries containing 33% antimicrobial active ingredient (Lenacil) were post added to a white, acrylic/silicone based outdoor paint free of biocides to give a total active ingredient concentration of 10000 and 1000 ppm respectively. KATHON™ 893T (100% OIT) and ROCIMA™ 200 (20% DCOIT) were post added to a white, acrylic/silicone based outdoor paint free of biocides to give a total active ingredient concentration of 10000 and 1000 ppm respectively. These paints were then diluted with an antimicrobial free acrylic/silicone based paint and mixed to prepare targeted concentrations of antimicrobial compounds for the testing. The total biocides concentrations tested were 125, 250, 500, 1000, 2000 and 5000 ppm. After biocides addition or dilution, the paints were mixed 90 seconds with the horse power shaker (AXEL 75M3372/Agitateur SO-10MI) until uniformity was achieved. Paints containing different antimicrobial compounds at the same levels were mixed together in order to obtain the desired ratio of antimicrobial compounds. After one day, the paints were applied to Schleicher & Schuell filter paper at 280 μm wet film thickness and dried for 3 days at room temperature avoiding direct exposure to sunlight. Square discs (1.6 cm×1.6 cm) were cut out from each panel and were used as the substrate for algal efficacy tests. This sample size allowed for an agar border when the sample disc was placed into the well of the test plate.

Algal Efficacy Testing:

Algal efficacy was tested according to modified ASTM 5589 which is a standard accelerated test method for determining resistance of various coatings (including paints) to algal defacement. To accommodate for high-throughput screening, this method was scaled down from petri dishes to 6-well plates. Bold Modified Basal Freshwater Nutrient Solution was used as growth medium. A single coated filter paper coupon was placed with a pair of sterile forceps at the center of the agar plug (on top) with the painted surface facing upwards. Algal inoculums were prepared by mixing equal concentrations ($1 \times 10^6$ cfu/ml) and equal volumes of exponentially growing algae cultures.

Algal Inoculums:

| Organisms | Strain No. | Type | Medium for testing |
| --- | --- | --- | --- |
| Chlorella sp. | ATCC 7516 | Unicellular Chlorophyte | Bold Modified Freshwater Solution |
| Stichococcus bacillaris | SAG 379-1a CCAP 379/1a | Unicellular or Filamentous Chlorophyte | Bold Modified Freshwater Solution |

Each well that contains a tested coupon was inoculated with 1750 μl of algal suspensions ($1 \times 10^6$ cfu/ml) making sure that the whole surface (paint film as well as the agar surrounding it) was evenly covered. The plates were incubated at room temp (21° C.-25° C.) with cyclic exposure to light and dark phases, for a period of three weeks.

At the end of the three week incubation period, the samples were scored for percent inhibition regarding visible algal growth compared to the blank sample (0% inhibition).

The Synergy Index calculation was performed as follows.

The SI is calculated based on F. C. Kull et al. method (Applied Microbiology, Vol. 9 (1961). In this study, SI was calculated based on the following formula with the minimum inhibitory concentration chosen based on the percent inhibitory exhibited by the individual antimicrobial against each microorganisms tested.

$$SI = Qa/QA + Qb/QB$$

Qa=the concentration of Antimicrobial A in the blend

QA=the concentration of Antimicrobial A as the only biocide

Qb=the concentration of Antimicrobial B in the blend

QB=the concentration of Antimicrobial B as the only antimicrobial

SI value of <1 in the formula indicates a synergism of the blended biocides exists.

Note: If any of the active with maximum concentration tested did not exhibit some inhibition, this maximum concentration is used to calculate the estimated SI and a sign of less than (<) is included to take into account that higher concentration of the active (Lenacil) is needed to achieve the targeted inhibition. The minimal targeted inhibition was set at 75%, meaning a coupon with at least 75% algal growth inhibition was considered as a pass.

Compositions listed below that contain both lenacil and one of OIT or DCOIT are examples of the present invention.

Test Results for OIT with Lenacil at 3 weeks were as follows:

| Pass level ≥75% inhibition | | |
|---|---|---|
| | Chlorella | Stichococcus |
| OIT | | |
| Total conc, ppm | 1000 | 500 |
| % inhibition | 95 | 90 |
| Lenacil | | |
| Total conc, ppm | 5000 | 5000 |
| % inhibition | 45 | 30 |
| 1 OIT:5Lenacil | | |
| Total conc, ppm | 1000 | 500 |
| % inhibition | 85 | 85 |
| SI | <0.33 | <0.25 |
| 1 OIT:2 Lenacil | | |
| Total conc, ppm | 500 | 500 |
| % inhibition | 75 | 80 |
| SI | <0.23 | <0.40 |
| 1 OIT:1 Lenacil | | |
| Total conc, ppm | 500 | 250 |
| % inhibition | 85 | 75 |
| SI | <0.30 | <0.28 |
| 2 OIT:1 Lenacil | | |
| Total conc, ppm | 500 | 250 |
| % inhibition | 90 | 80 |
| SI | <0.37 | <0.35 |
| 5 OIT:1 Lenacil: | | |
| Total conc, ppm | 1000 | 250 |
| % inhibition | 95 | 95 |
| SI | <0.87 | <0.42 |

OIT + Lenacil at ratio 1:5 to 5:1 exhibited a synergy.

| Pass level ≥75% inhibition | | |
|---|---|---|
| | Chlorella | Stichococcus |
| DCOIT | | |
| Total conc, ppm | 1000 | 1000 |
| % inhibition | 85 | 95 |
| Lenacil | | |
| Total conc, ppm | 5000 | 5000 |
| % inhibition | 30 | 70 |
| 1 DCOIT:5Lenacil | | |
| Total conc, ppm | 2000 | 2000 |
| % inhibition | 80 | 75 |
| SI | <0.67 | <0.67 |
| 1 DCOIT:2 Lenacil | | |
| Total conc, ppm | 2000 | 1000 |
| % inhibition | 90 | 75 |
| SI | <0.93 | <0.47 |
| 1 DCOIT:1 Lenacil | | |
| Total conc, ppm | 2000 | 1000 |
| % inhibition | 95 | 90 |
| SI | <1.20 | <0.60 |
| 2 DCOIT:1 Lenacil | | |
| Total conc, ppm | 1000 | 1000 |
| % inhibition | 90 | 95 |
| SI | <0.73 | <0.73 |
| 5 DCOIT:1 Lenacil | | |
| Total conc, ppm | 1000 | 1000 |
| % inhibition | 90 | 95 |
| SI | <0.87 | <0.87 |

DCOIT + Lenacil at ratio 1:5 to 5:1 exhibited a synergy.

The invention claimed is:

1. A synergistic antimicrobial composition comprising lenacil and one of 4,5-dichloro-2-n-octyl-4-isothiazolin-3-one or 2-n-octyl-4-isothiazolin-3-one.

2. The synergistic antimicrobial composition of claim 1, wherein the synergistic antimicrobial composition comprises 4,5-dichloro-2-n-octyl-4-isothiazolin-3-one or 2-n-octyl-4-isothiazolin-3-one, and wherein the weight ratio of the 4,5-dichloro-2-n-octyl-4-isothiazolin-3-one or 2-n-octyl-4-isothiazolin-3-one to lenacil is from 1:5 to 5:1.

3. A synergistic antimicrobial composition comprising lenacil and 4,5-dichloro-2-n-octyl-4-isothiazolin-3-one and 2-n-octyl-4-isothiazolin-3-one wherein the weight ratio of the 4,5-dichloro-2-n-octyl-4-isothiazolin-3-one and 2-n-octyl-4-isothiazolin-3-one to lenacil is from 1:10 to 10:1.

4. A method of inhibiting the growth of or controlling the growth of microorganisms in a building material, the method comprising the step of adding the synergistic antimicrobial composition of claim 2 to the building material.

5. A coating composition comprising the synergistic antimicrobial composition of claim 1.

6. A coating composition comprising the synergistic antimicrobial composition of claim 2.

7. A dry film made by a process comprising applying a layer of the coating composition of claim 6 to a substrate and drying the coating composition or allowing the coating composition to dry.

* * * * *